(12) United States Patent
Nef et al.

(10) Patent No.: US 9,084,540 B2
(45) Date of Patent: Jul. 21, 2015

(54) EYE EXAMINING INSTRUMENT

(71) Applicant: Haag-Streit AG, Koeniz (CH)

(72) Inventors: Tobias Nef, Bern (CH); René Mueri, Herzogenbuchsee (CH); Philipp Gloor, Wuennewil (CH); Urs Mosimann, Bern (CH)

(73) Assignee: HAAG-STREIT AG, Koeniz (CH)

( * ) Notice: Subject to any disclaimer, the term of this patent is extended or adjusted under 35 U.S.C. 154(b) by 50 days.

(21) Appl. No.: 13/959,295

(22) Filed: Aug. 5, 2013

(65) Prior Publication Data
US 2014/0036230 A1 Feb. 6, 2014

(30) Foreign Application Priority Data
Aug. 6, 2012 (CH) ..................................... 1286/12

(51) Int. Cl.
A61B 3/024 (2006.01)
A61B 3/10 (2006.01)
A61B 3/032 (2006.01)
A61B 3/00 (2006.01)

(52) U.S. Cl.
CPC .............. A61B 3/024 (2013.01); A61B 3/0008 (2013.01); A61B 3/032 (2013.01); A61B 3/10 (2013.01)

(58) Field of Classification Search
CPC .................................. A61B 3/024; A61B 3/10
USPC ................................................... 351/224–226
See application file for complete search history.

(56) References Cited

U.S. PATENT DOCUMENTS 6,327,020 B1 * 12/2001 Iwata ............................. 352/69
2005/0024722 A1 2/2005 Agostinelli et al.

FOREIGN PATENT DOCUMENTS

| DE | 10350836 A1 | 6/2005 |
| EP | 2260753 A1 | 12/2010 |
| JP | 2001-42260 * | 2/2001 |
| JP | 2008-3132 A | 1/2008 |
| WO | WO 99/41641 A1 | 8/1999 |

* cited by examiner

Primary Examiner — Jordan Schwartz
(74) Attorney, Agent, or Firm — Birch, Stewart, Kolasch & Birch, LLP

(57) ABSTRACT

An eye examining instrument comprises a projection device and a concave screen. The eye examining instrument furthermore comprises a convex reflector, wherein an image can be projected by the projection device onto the convex reflector and reflected by the convex reflector onto the concave screen.

16 Claims, 2 Drawing Sheets

EYE EXAMINING INSTRUMENT

TECHNICAL FIELD

The invention relates to an eye examining instrument, more particularly a perimeter, comprising a projection device and a concave screen. The invention furthermore relates to an imaging method using an eye examining instrument.

PRIOR ART

The term "perimetry" is understood to mean the systematic examination of the visual field, more particularly the measuring thereof. Using it, it is possible to determine outer and inner boundaries of the visual field and, moreover, the sensitivity of the visual system in the perceived space. Such instruments are well known. In the method, the patient fixes onto a point on a screen while optical stimuli are successively projected onto various locations of the screen. The visual field can be constructed on the basis of the optical stimuli detected by the patient.

By way of example, DE 103 50 836 B4 (Frauenhofer) discloses a digital projector for perimetry and a corresponding perimeter. The projector can be used to generate digital images, which completely or almost completely fill the human field of vision, wherein these images predeterminable by digital data can be within large boundaries of arbitrary type and time varying, without complicated mechanical image updating being necessary. Here, the patient's head is placed next to an exit pupil of the projector. The projection area is hemispherical. The exit pupil is arranged level with the centre of the sphere and the eye to be examined is arranged laterally offset from the centre of the sphere. The distortion perceived by the eye in the process is negligible. The projector has three image-producing elements, which are embodied as LCoS displays.

The known eye examining instruments are disadvantageous in that they require much space.

DESCRIPTION OF THE INVENTION

It is an object of the invention to develop an eye examining instrument belonging to the technical field described at the outset, which has a particularly compact design.

The solution to the object is defined by the features of claim 1. According to the invention, the eye examining instrument furthermore comprises a convex reflector, wherein an image can be projected by the projection device onto the convex reflector and reflected by the convex reflector onto the concave screen.

As a result of using a convex reflector, the eye examining instrument can have a particularly compact design. Moreover, the eye examining instrument can be produced in a cost-effective manner and is simple to operate. At least some of the light projected by the projection device is preferably reflected by the reflector. The percentage of the light projected by the projection device which is reflected by the reflector preferably is high, in particular more than 50%, particularly preferably over 80%.

The concave screen, also referred to as a cupola, is preferably shaped in such a way that the field of vision can be examined in a horizontal and vertical angle range of +/−90°.

As a result of the occurring distortions of the image, the projection onto a concave screen requires a transformation of the image to be projected. These conversions are sufficiently well known, for example from the book: Bourke, P., Spherical mirror: a new approach to hemispherical dome projection (Planetarian, 2005: 34(4), 6-9) for hemispherical screens. However, the conversion for differently shaped concave screens and convex reflectors are known to a person skilled in the art and can, if need be, also be brought about iteratively by virtue of the projected image being compared to the image to be projected after each adaptation until the quality meets the requirements.

In an imaging method using such an eye examining instrument, the projection device projects a beam onto the convex reflector and the beam is reflected by the convex reflector onto the concave screen and imaged on the concave screen. The original image is initially transformed in a suitable fashion, subsequently projected onto the reflector and reflected into the concave screen thereby. Together with the image, test objects such as points or small images can be projected into an image, e.g. a bird into a landscape or the like. It is additionally possible to superpose interfering images, such as e.g. geometric figures, triangles or the like. Finally, it is also possible to vary the sizes of the points, small images and interfering images, as well as contrast amongst the objects, the background image and the timing. It is possible to define a difficulty level by means of a suitable selection of the individual parameters (type of objects, background image, timing, contrast etc.). The subject can operate a pushbutton when he sees the point or the small image. It is possible to establish the visual field of the subject on the basis of the reaction time and the location of the point or small image.

The pushbutton (e.g. a mouse) is preferably linked to the projector via a computer. However, the measured reaction time is composed of the system delay and the real reaction time of the subject. Hence use is preferably made of a computer which has a shorter delay time. Alternatively, it is possible to measure the delay time of the system continuously, for example by virtue of a light point being projected onto the screen outside of the visual field when a test object is projected. Using a high-frequency light sensor (e.g. with a measurement frequency of 1000 Hz), it is possible to measure and eliminate the delay time of the computer thereby.

The projection device can preferably be used to project an areal image, more particularly a screen-filling image. Here, an "areal image" means an image which can be projected onto the screen statically or moving as a film by means of the projection device. The areal image can thereby have at least two regions with at least differing contrasts or wavelengths (or colours) such that it is possible, for example, to project colour images. The convex reflector can preferably be used to project the light emitted by the projection device onto the whole screen. This is how it is possible, for example, to project films onto the screen.

In some variants, it is also possible to project merely an image which comprises one image point with precisely one contrast and one wavelength instead of the areal image.

The concave screen preferably has the shape of an inner side of a spherical cup, more particularly a hemisphere. The concave screen is preferably shaped in such a way that the field of vision can be examined in a horizontal and vertical angle range of +/−90°. By way of example, this is achieved by a hemisphere. An image conversion can also take place more easily by selecting a hemispherical shape.

However, in some variants, it is also possible to provide for other shapes, such as the shape of a rotational paraboloid, a rotational ellipsoid half or the like. The shape can also be established empirically and, as a result, does not follow an ideal mathematical function. Nor does it have to be rotationally symmetric.

However, the screen is preferably shaped in such a way that no shadows can be created during the projection. The image can then be adapted e.g. iteratively by virtue of the image projected onto the screen being compared to the original image in each case and the parameters being subsequently adapted.

The convex reflector preferably has the shape of an outer side of a spherical cup section, in particular the shape of a spherical cup half. This once again simplifies the conversion of the image material.

The shape of the reflector can likewise have the shape of a rotational paraboloid, a rotational ellipsoid half or the like.

The projection device preferably has a projection axis, which includes an angle of between 70° and 110°, preferably of between 80° and 100°, in particular of 90°, with the spherical cup height of the screen. Here, the term projection axis is understood to mean an average beam direction from the projection device, for example the direction of a vector sum of the emitted beams. As a result of the fact that the projection axis includes said angle with the spherical cup height, the eye examining instrument can have a particularly compact design since the projection device for example does not have to be positioned parallel to the viewing direction of the patient, i.e. next to the patient's head. Hence, this moreover results in much design freedom for the arrangement of the projection device. An overall length in the direction of the spherical cup height of the screen of the eye examining instrument can thereby be minimized.

The projection device is preferably arranged in the edge region of the concave screen. This makes a particularly compact eye examining instrument. The arrangement in the edge region is advantageous in that the projection is not hindered by the patient's head, as is the case in known instruments, in which the projection device is arranged next to the patient's head. This is because in the latter case, a compromise is made in each case since, in actual fact, both the projection device and the patient's head should ideally be positioned at the spherical cup height. Nor is the patient blinded by the projection device, as a result of which particularly simple handling is achieved.

In some variants, the projection device can also be aligned outside of the aforementioned angles and angle ranges. By way of example, provision can be made for an opening in the screen, through which the image is projected in the direction of the reflector and then reflected back onto the screen by the latter. In this case, the angle would lie in a region between 0° and 20°. Furthermore, as mentioned above, the projection device can be positioned next to the patient's head. However, it is also feasible for two or more projection devices to be provided, which respectively project the image onto one half or several portions of the screen, which can also overlap. In this case, it is also possible to provide more obtuse angles in the region of more than 110°. Overlaps can be advantageous in portions in which the area ratio of the projection portion on the screen to the corresponding reflection portion on the reflector is large and therefore the light intensity tends to be low.

The convex reflector is preferably arranged in the edge region of the concave screen. Using this position, a projection of an image filling the screen is easily achieved using precisely one projection device. This largely prevents the patient from seeing the projection device during the eye examination and possibly being distracted. Moreover, this achieves a compact design of the eye examining instrument.

A person skilled in the art knows that the convex reflector can also be placed elsewhere in other variants, particularly if several projection devices are used as well. The position of the reflector also largely depends on the position of the projection device.

In order to create an aesthetic finish, an annular stop is preferably provided as termination of the screen, in which the patient places his head. As a result of being able to shield stray light by the annular stop, it is moreover possible to improve the image contrasts.

It is naturally also possible to dispense with the annular stop.

The convex reflector and the projection device are preferably arranged opposite to one another in the edge region of the concave screen. This enables a projection of the image with symmetric brightness. The convex reflector is preferably arranged in the region of the patient's chin during use of the eye examining instrument.

This arrangement is advantageous since, in relation to the concave screen, a typical visual field is restricted by the eyebrows in the upper region, i.e. in the vertical upper region in respect of a horizontal viewing direction. The visual-field angle is typically approximately 50° above the horizontal and approximately 80° below the horizontal, while the visual-field angle is approximately 90° to the perpendicular in each case. It is therefore expedient to arrange the projection device, which requires the greatest amount of volume, in this region. On the other hand, if the convex reflector had larger dimensions than the projection device, the reflector would preferably be arranged in this region. In this case, the projection device would a be arranged in the region of the chin. In principle, the further positioning options are also feasible.

In some variants, it is also possible to provide for an arrangement of the reflector and the projection device in the edge region of the screen without being arranged opposite to one another.

The convex reflector is preferably arranged within a space spanned by the concave screen. This makes a compact eye examining instrument. As mentioned above, this makes it possible to use the unused space in the upper region of the screen, i.e. opposite an optionally placed chin rest.

In some variants, the reflector can also be arranged outside of the space spanned by the screen, i.e. in the direction of the cup height of the screen away from the screen and hence outside of the screen.

The projection device is preferably also arranged within a space spanned by the concave screen. This in turn achieves a compact design of the eye examining instrument.

In some variants, the projection device can also be arranged outside or partially outside of the space spanned by the concave screen. In principle, when positioning the projection device, it is sufficient for it to be possible to project an image onto the reflector thereby. However, if the projection device is positioned outside of the screen but in the same cup sectional plane of the screen, an opening can be provided in the screen, through which the projection can take place. If the projection device is positioned outside of the screen in the direction of the cup height of the screen, care should be taken that the head of the patient is not positioned in the beam path between the projection device and the reflector during the examination.

The projection device is preferably embodied as LED projector or as laser projector. These projectors are particularly preferred since they are available in compact form and have a sufficient light output.

The laser projector in particular is advantageous in that the image is always in focus and hence it is possible to project in-focus images onto almost arbitrarily shaped projection surfaces, particularly in the case of a projection onto the concave screen via a convex reflector. No focusing is necessary. Moreover, it is possible to achieve a high contrast and a high gamut.

The advantage of the LED projector is that a high luminosity can be achieved. No particular design is necessary for the operation. There is no direct danger to the eye.

The projection device preferably has a luminance of between 5 and 10 cd/m², more particularly of approximately 7.5 cd/m². The luminance can naturally also be higher or lower in other variants. The upper and lower boundaries depend substantially on the projection area and the light yield during the reflection at the reflector.

The eye examining instrument can furthermore have a camera, by means of which the position of the eyes can be monitored.

The eye examining instrument can furthermore also be used for therapy purposes, in order to train and improve the visual field, for example after an accident, after a stroke, etc.

Further advantageous embodiments and combinations of features of the invention emerge from the following detailed description and the totality of the patent claims.

BRIEF DESCRIPTION OF THE DRAWINGS

In the drawings used to explain the exemplary embodiment.

In principle, in the figures, the same parts have been provided with the same reference signs.

Ways of Implementing the Invention

Figure 1:
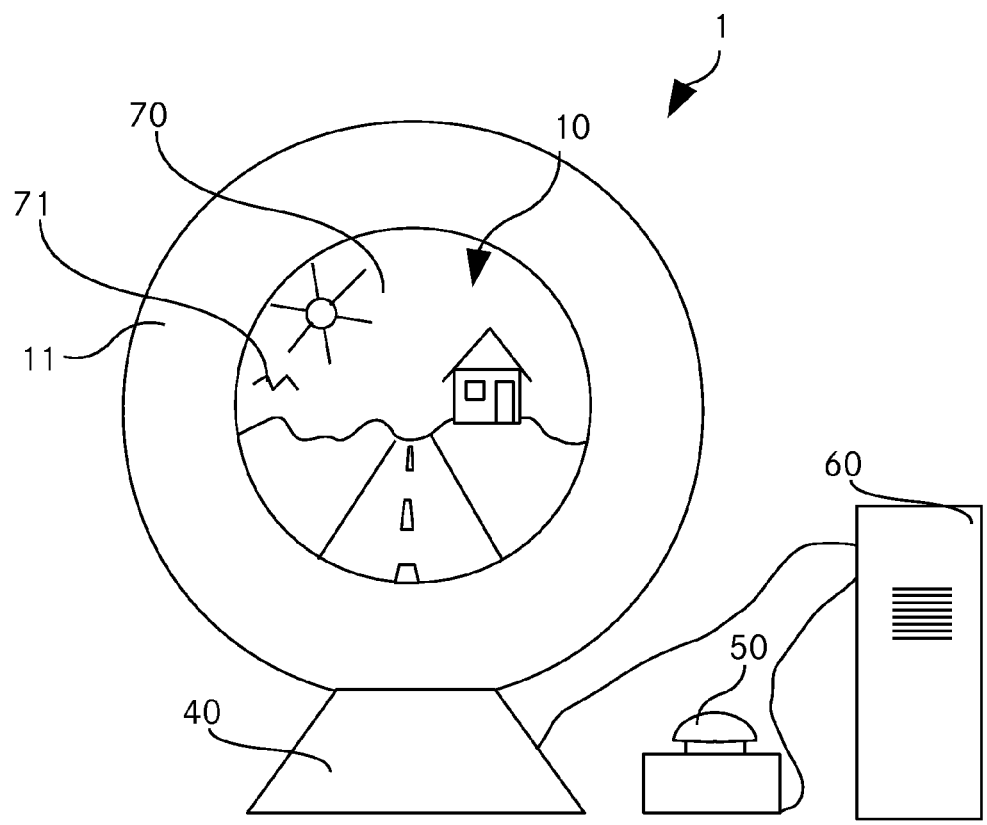
FIG. 1 shows a front view in the direction of the cup height of the screen of a schematic perimeter.

FIG. 1 shows a front view in the direction of the cup height of the hemispherical screen 10 of the schematic perimeter 1. The perimeter "Octopus 900" by Haag Streit AG, Kööniz (CH) can serve as a basis for the perimeter 1, wherein, substantially, there have been modifications to the projector and the reflector and the data processing.

The perimeter 1 comprises a housing 40, on which the hemispherical screen 10 has been assembled. The hemispherical screen 10 (referred to as screen 10 below) has a diameter of approximately 60 cm. Attached to the front side of the screen 10 is a stop in the form of an annular disc cover 11. During use, a patient or subject positions his head within the opening of the annular disc cover 11. To this end, the perimeter 1 comprises a displaceable chin rest and a stop for the forehead such that the head can be positioned and aligned accurately (not illustrated). Through the opening of the annular disc cover 11, it is possible to identify, projected onto the screen 10, an image 70, which furthermore comprises a test object 71.

Finally, FIG. 1 shows a pushbutton 50 and a computer 60, wherein the pushbutton 50 is connected to the computer 60 and the computer 60 is connected to the perimeter 1.

During the method, the head of the patient is initially positioned on the chin rest and the forehead stop, centrally in the opening of the annular disc cover 11 with respect to the centre of the two eyes. Subsequently, the patient fixes on a central point (e.g. the end of the road in the image 70) and, by pressing the pushbutton 50, lets it be known when he has identified the test object 71 in the projected image. The computer is used to evaluate the established data in order to construct the visual field of the patient.

Figure 2:
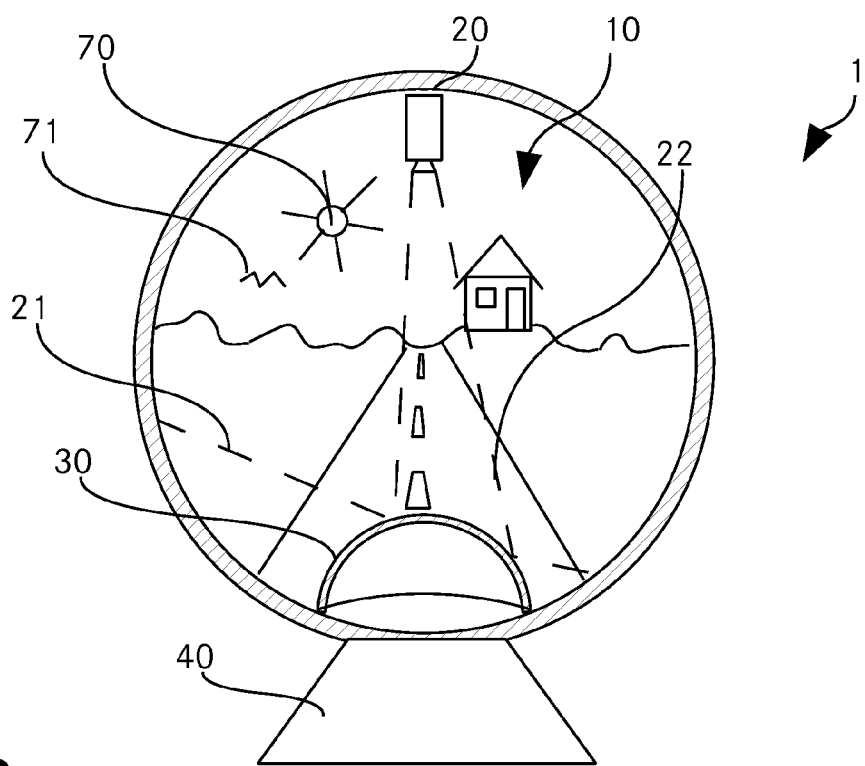
FIG. 2 shows a sectional image of the perimeter across the cup height of the screen of the perimeter as per FIG. 1.

FIG. 2 shows a sectional image of the perimeter 1 across the cup height of the hemispherical screen 10 of the perimeter 1 as per FIG. 1. In contrast to FIG. 1, it is now possible to identify the projector 20 and the spherical mirror 30, which are covered by the annular disc stop 11 in FIG. 1, in FIG. 2. In the present case, the projector 20 is designed as a laser projector and arranged in a vertically upper region of the screen 10. The spherical mirror 30 is arranged opposite thereto, i.e. in a vertically lower region. Said mirror has the shape of a quarter-sphere, wherein there can be certain deviations from an ideal quarter-sphere or a 90° sphere cut. A light beam 21, 22 emitted by the projector is reflected at the spherical mirror 30 and projected onto the screen 10. So that the image 70 and the test object 71 are not illustrated in a distorted manner on the hemispherical screen 10, there is a suitable conversion or transformation of the image data prior to the projection.

Figure 3:
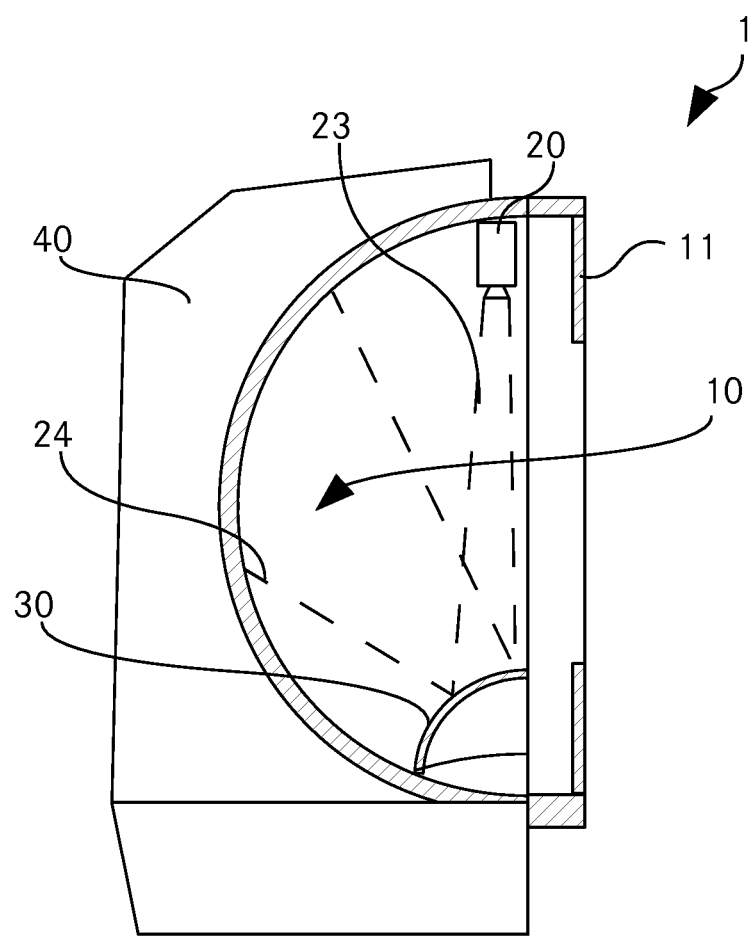
FIG. 3 shows a side view of a sectional image of the perimeter in the direction of the cup height of the screen.

FIG. 3 shows a side view of a sectional image of the perimeter 1 in the direction of the cup height of the screen 10. In this illustration, the hemisphere-shaped screen 10 with the annular disc cover 11 is visible. Once again, two beams 23, 24 are illustrated for illustrative purposes, which beams are reflected at the spherical mirror 30 after being emitted by the projector 20 and projected onto the screen.

In conclusion, according to the invention, an eye examining instrument has been developed, which is cost-effective in production, compact and easy to operate.

The invention claimed is:

1. Eye examining instrument comprising:
a projection device;
a concave screen; and
a convex reflector,
wherein an image can be projected by the projection device onto the convex reflector and reflected by the convex reflector onto the concave screen,
wherein the convex reflector and the projection device are arranged opposite to one another in the edge region of the concave screen.

2. Eye examining instrument according to claim 1, characterized in that the projection device can be used to project an areal image over the whole concave screen.

3. Eye examining instrument according to claim 1, characterized in that the concave screen has the shape of an inner side of a spherical cup.

4. Eye examining instrument according to claim 1, characterized in that the convex reflector has the shape of an outer side of a spherical cup section.

5. Eye examining instrument according to claim 3, characterized in that the projection device has a projection axis, which includes an angle of between 70° and 110° with the spherical cup height of the screen.

6. Eye examining instrument according to claim 1, characterized in that the projection device is arranged in the edge region of the concave screen.

7. Eye examining instrument according to claim 1, characterized in that the convex reflector is arranged in the edge region of the concave screen.

8. Eye examining instrument according to claim 1, characterized in that the convex reflector is arranged within a space spanned by the concave screen.

9. Eye examining instrument according to claim 1, characterized in that the projection device is arranged within a space spanned by the concave screen.

10. Eye examining instrument according to claim 1, characterized in that the projection device is embodied as LED projector or as laser projector.

11. Imaging method using an eye examining instrument according to claim 1, wherein the projection device projects a beam onto the convex reflector and the beam is reflected by the convex reflector onto the concave screen and imaged on the concave screen.

12. Eye examining instrument according to claim 2, characterized in that the projection device can be used to project a screen-filling image.

13. Eye examining instrument according to claim 3, characterized in that the concave screen has the shape of a hemisphere.

14. Eye examining instrument according to claim 4, characterized in that the convex reflector has the shape of a spherical cup half.

15. Eye examining instrument according to claim 5, characterized in that the projection device has a projection axis, which includes an angle of between 80° and 100° with the spherical cup height of the screen.

16. Eye examining instrument according to claim 15, characterized in that the projection device has a projection axis, which includes an angle of 90°, with the spherical cup height of the screen.

* * * * *